United States Patent [19]

Rose

[11] Patent Number: 4,512,995

[45] Date of Patent: Apr. 23, 1985

[54] PHENOXYALKENYLPYRIDINE DERIVATIVES AND FUNGICIDAL METHODS OF USE

[75] Inventor: Allan F. Rose, Richmond, Calif.

[73] Assignee: Chevron Research Company, San Francisco, Calif.

[21] Appl. No.: 455,190

[22] Filed: Jan. 3, 1983

[51] Int. Cl.³ .................... C07D 213/30; A01N 43/40
[52] U.S. Cl. .................................. 514/277; 546/339; 546/344
[58] Field of Search ............... 542/427; 546/339, 344; 424/263

[56] References Cited

U.S. PATENT DOCUMENTS 4,262,000  4/1981  Holmwood et al. ................ 424/263

Primary Examiner—Alan L. Rotman
Attorney, Agent, or Firm—S. R. LaPaglia; T. G. DeJonghe; L. S. Squires

[57] ABSTRACT

3-[2-aryloxy-3-hydroxy-3-phenyl or 3-t-butylprop-1-enyl]pyridine and derivatives thereof are disclosed. These compounds are useful as fungicides, especially agricultural fungicides.

19 Claims, No Drawings

PHENOXYALKENYLPYRIDINE DERIVATIVES AND FUNGICIDAL METHODS OF USE

BACKGROUND OF THE INVENTION

This invention relates to certain fungicidal phenoxyalkenylpyridine derivatives and to methods of preparing such derivatives. In a further aspect the invention relates to the application of said derivatives as fungicides.

U.S. Pat. No. 4,262,000 describes certain 3-phenoxy-hydroxyalkanylpyridine and 3-phenoxy-ketoalkenylpyridine derivatives as having fungicidal activity.

SUMMARY OF THE INVENTION

The present invention provides compounds having fungicidal activity and having especially excellent activity against bean powdery mildew pathogen and celery late blight pathogen. Moreover, certain of the compounds are active against bean rust pathogen. This is surprising since the corresponding saturated alkyl analogs and keto analogs of the present compounds, such as described in U.S. Pat. No. 4,262,000, although exhibiting activity against bean powdery mildew pathogen fail to exhibit any significant eradicant activity against celery late blight pathogen nor against bean rust pathogen. The present compounds thus afford a significant and unexpected advantage in the treatment of these diseases.

The compounds of the present invention can be represented by the following generic formula:

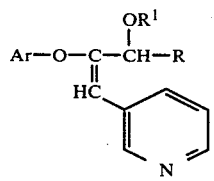

wherein

Ar is phenyl, naphthyl, substituted phenyl or substituted naphthyl in each case substituted with one or two substituents independently selected from the group of halo, lower alkyl, lower alkoxy, or phenyl;

R is phenyl or the group having the formula:

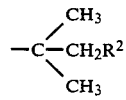

wherein $R^2$ is hydrogen, alkyl, having 1 through 4 carbon atoms, hydroxy, or halo;

and $R^1$ is hydrogen, lower alkyl, benzyl, allyl, haloallyl, having 1 or 2 halo substituents independently selected from the group of fluoro, chloro, bromo and iodo, or lower alkyl carbonyl;

Compatible salts of the compounds of Formula I are also encompassed within the invention.

The compounds of the invention exist as geometric isomers with respect to the double bond. Moreover, the compounds also have an asymmetric carbon atom and thus can also exist as optical isomers. The above Formula I is intended to represent both the respective individual geometric and optical isomers and also mixtures thereof, and the respective individual as well as isomer mixtures are encompassed within the invention.

The invention also provides processes for preparing the above compounds.

In a further aspect, the invention provides fungicidal compositions comprising a compatible carrier and an amount of the compound of Formula I effective to prevent or arrest the growth of fungi or eradicate fungi.

In another aspect, the invention provides a method for controlling fungi which comprises applying an amount of the compound of Formula I, effective to prevent or arrest the growth of fungi or eradicate fungi to such fungi or to the potential growth medium of such fungi (e.g., vegetation).

The invention will be further described hereinbelow.

FURTHER DESCRIPTION OF THE INVENTION AND PREFERRED EMBODIMENTS

Illustrations of typical compounds of Formula I of the invention, can be had by reference to Examples 1, 2, and 3 (Table I) set forth hereinbelow on Pages 13, and 14.

In part based on their fungicidal properties, the preferred compounds, in terms of their substituents, are those wherein Ar is 4-halophenyl, especially 4-chlorophenyl, or 2,4-dihalophenyl, especially 2,4-dichlorophenyl, or biphenyl. The preferred R substituent is t-butyl. The preferred $R^1$ substituent is hydrogen.

The preferred compounds are those having one or more of the above preferred substituents and most preferably having a preferred substituent at each respective position.

Definitions

As used herein, the following terms have the following meanings, unless expressly stated to the contrary.

The term "alkyl" refers to both straight- and branched-chain alkyl groups. Generally, such alkyl groups contain from 1 through 12 carbon atoms.

The term "lower alkyl" refers to both straight- and branched-chain alkyl groups having from 1 through 6 carbon atoms and includes primary, secondary and tertiary alkyl groups. Typical lower alkyls include, for example, methyl, ethyl, n-propyl, isopropyl, n-butyl, t-butyl, n-hexyl, and the like.

The term "halo" or "halogen atom" refers to the groups fluoro, chloro, bromo and iodo.

The term "alkoxy" refers to the group $R^6O-$ wherein $R^6$ is alkyl.

The term "lower alkoxy" refers to the alkoxy groups having from 1 through 6 carbon atoms and includes, for example, methoxy, ethoxy, t-butoxy, hexoxy, and the like.

The term "lower alkyl carbonyl" refers to the group having the formula

wherein $R^{6'}$ is lower alkyl.

The term "lower alkoxycarbonyl" refers to the group

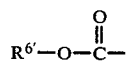

wherein $R^{6'}$ is lower alkyl.

The term "compatible salt" refers to salts of the parent compound which do not significantly adversely effect the fungicidal properties of the parent compound and are substantially non-phytotoxic at the appropriate fungicidal dosage.

The term "fungicidal" is a broad term and refers to either or both preventative (prevents fungicidal infections) and eradicant (fungalstatic—prevents the growth of fungi ultimately producing destruction of the fungus through failure to reproduce and more rarely curatic: directly causes the destruction of the fungus).

The term "compatible carrier" refers to substances which can be mixed with the fungicidal compounds of the present invention which do not significantly adversely affect the properties of the active compound save to dilute it and are substantially non-phytotoxic. Examples of suitable compatible carriers are given in the Utility section set forth hereinbelow.

Synthesis

The compounds of Formula I can be prepared by the following process schematically represented by the following overall reaction equation:

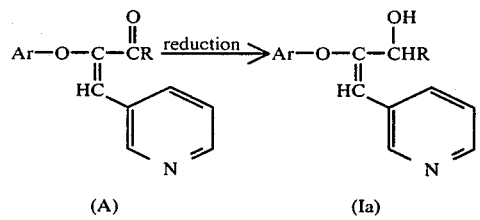

wherein Ar and R are as defined hereinabove.

This process can be conveniently effected by contacting compound (A) with a keto reducing agent under reactive conditions, preferably in an inert organic solvent. Typically, this process is conducted at temperatures in the range of about from −10° to 100° C., preferably about from 0° to 20° C. for about from 0.5 to 5 hours, preferably about from 0.5 to 1 hour using about from 1 to 4, preferably about from 1 to 1.5 mole equivalents of the reducing agent per mole of compound A. Suitable inert organic solvents which can be used include, for example, methanol, methylene chloride, ethanol, isopropanol, tetrahydrofuran, and the like and compatible mixtures thereof. Water and compatible mixtures of the above solvents with water can also be used. Suitable reducing agents which can be used include, for example, sodium borohydride, sodium cyanoborohydride, lithium aluminum hydride, and the like.

The ethers of Formula I wherein $R^1$ is alkyl benzyl, ally, or haloallyl can be conveniently prepared via the following schematically represented process:

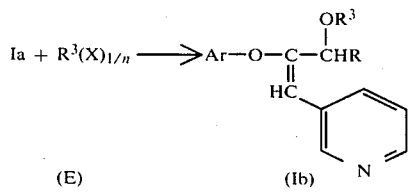

wherein $R^3$ is lower alkyl, benzyl, allyl, or haloallyl and X is an anion (e.g. halide, sulfate) and n is its valence.

This process can be effected by contacting compound Ia with compound (E) under reactive conditions preferably in an inert organic solvent.

Typically this process is conducted at temperatures in the range of about from −20° to 100° C., preferably about from 0° to 20° C., for about from 0.5 to 12 hours, preferably about from 0.5 to 1.5 hours using about from 1 to 3, preferably about from 1 to 1.2 mole equivalents of compound $R^3(X)_{1/n}$ per mole of compound Ia. Suitable inert organic solvents which can be used include, for example, tetrahydrofuran, dimethylformamide, toluene, and the like and compatible mixtures thereof.

The esters of Formula I wherein $R^1$ is lower alkyl carbonyl can be conveniently prepared via the following schematically represented process:

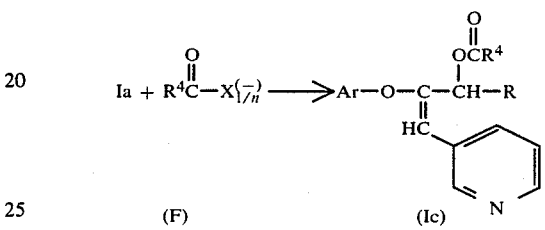

wherein $R^4$ is lower alkyl and X is an anion (e.g. halide, imidazole, hydroxy, oxycarbonylalkyl, etc.) and n is its valence.

This process can be effected by contacting compound Ia with compound F under reactive conditions preferably in an inert organic solvent and in the presence of a base.

Typically this process is conducted at temperatures in the range of about from −10° to 100° C., preferably about from 0° to 40° C. for about from 0.5 to 12 hours, preferably about from 0.5 to 1.5 hours using from about 1 to 3, preferably from 1 to 1.1 mole equivalents of compound F per mole of compound Ia and in the presence of from about 1 to 4, preferably from about 1 to 1.5 mole equivalents of base per mole of compound Ia. Suitable bases which can be used include, for example, triethyl amine, pyridine, sodium or potassium bicarbonate, sodium or potassium hydroxide, and the like. Suitable inert organic solvents which can be used include, for example, toluene, benzene, dichloromethane, chloroform, tetrahydrofuran, dioxane and the like and compatible mixtures thereof.

The starting materials of Formula A are generally known compounds and can be prepared by known procedures, such as for example described in U.S. Pat. No. 4,262,000. The compounds of Formula A can also be prepared by the following process schematically represented by the following overall reaction equations:

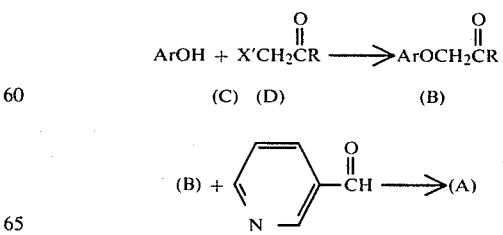

wherein X' is chloro or bromo and Ar and R are as defined hereinabove.

The first step of this process can be effected by contacting compound C with compound D under reactive conditions preferably in water and/or an inert organic solvent and in the presence of a base. This process is typically conducted at temperatures in the range of about from 0° to 150° C., preferably 60° to 100° C. for about from 1 to 10 hours, preferably 1 to 4 hours using about from 1 to 2 moles, preferably 1 mole of compound D per mole of compound C.

Suitable inert organic solvents which can be used include, for example, methanol, ethanol, toluene, and the like and compatible mixtures thereof. Water can also be used as a solvent or diluent.

The use of a base generates the anion of compound C which is a better nucleophile in the displacement of X′ from compound D. Preferably about one mole equivalent of base is used per mole equivalent of compound C. Suitable base which can be used include sodium methoxide, sodium hydroxide, potassium hydroxide, sodium carbonate, sodium hydride, and the like.

The second step of this process can be effected by contacting compound B with 3-pyridinecarboxaldehyde under reactive conditions, preferably in an inert organic solvent and in the presence of base. Typically, this reaction is conducted at temperatures in the range of about from 0° to 100° C., preferably about from 10° to 25° C. for about from 1 to 48 hours, preferably 12 to 24 hours using about from 1 to 3 moles, preferably 1 to 1.5 moles of 3-pyridinecarboxaldehyde per mole of compound B.

Suitable inert organic solvents which can be used include, for example, methanol, ethanol, methylene chloride, toluene, and the like and compatible mixtures thereof.

Suitable bases which can be used include, for example, sodium hydroxide, potassium hydroxide, sodium methoxide, sodium ethoxide, and the like. Typically about from 0.01 to 1.5 mole equivalents, preferably 0.01 to 0.1 equivalents, of base are used per mole of compound B.

The anion salts of the compounds of Formula I can be prepared by reacting the free base of Formula I with an acid having the appropriate anion or by ion exchange of one salt of Formula I with the appropriate anion exchange resin. The procedures for preparing salts described in U.S. Pat. No. 4,262,000, Column 12, which procedures are hereby incorporated by reference, can also be applied to prepare the salts of the present invention.

Unless expressly stated to the contrary, it is preferred to separate the desired product of the above process steps before proceeding with the next step in the process. Any suitable separation procedure can be used to effect separation such as, for example, where appropriate, extraction, filtration, evaporation, distillation, chromatography, etc. Illustrations of suitable separation procedures can be found in the appropriate example given hereinbelow.

Generally, the reactions described above are conducted as liquid-phase reactions and hence pressure is generally not significant except as it affects temperature (boiling point) where reactions are conducted at reflux. Therefore, these reactions are generally conducted at pressures of from 300 to 3000 mm mercury and conveniently are conducted at about atmospheric or ambient pressure.

It should also be appreciated that where typical or preferred process conditions (e.g., reaction temperatures, times, mole ratios of reactants, solvents, etc.) have been given, that conditions above or below these ranges may also be used in some instances but generally with poorer results or economies. Optimum conditions may vary with the particular reagents or organic solvents used but can be determined by routine optimization procedures.

Where optical isomer mixtures are obtained, the respective optical isomers can be obtained by conventional resolution procedures, for example, by reacting the isomer mixture with an optically active acid which will yield a mixture of optical salts, of the desired compound, which can be resolved by conventional procedures (e.g., crystallization) into the respective plus and minus optical salts. The respective geometric isomers can be obtained by conventional procedures based on differences in physical properties.

Utility

The compounds of the present invention exhibit fungicidal activity and especially preventative activity against plant fungal diseases. The compounds are especially effective against powdery mildew fungal diseases caused by organisms such as *Erysiphe polygoni* and also against celery late blight producing organisms such as *Septoria apii*. Moreover, certain of the present compounds are highly effective against rust causing organisms such as *Uromyces phaseoli tipica*.

The compounds of the invention can be applied in fungicidally effective amounts to fungi and/or their habitats, such as vegetative hosts and non-vegetative hosts, e.g., animal products. The amount used will, of course, depend on several factors such as the host, the type of fungus and the particular compound of the invention. As with most fungicides, the compounds of the invention are usually not applied as pure compounds, but are generally incorporated with carriers to facilitate dispersion of the active fungicidal compounds. Generally, the carriers are biologically inert. The fungicides of the invention can be formulated and applied as granules, powdery dusts, wettable powders, emulsifiable concentrates, solutions, or as any of several other known types of formulations, depending on the desired mode of application.

Wettable powders are finely divided particles which disperse readily in water or other dispersant. These compositions normally contain from about 5% to 80% fungicide, and the rest carriers, dispersing agents, emulsifying agents and/or wetting agents. The powder may be applied to the soil as a dry dust, or as a suspension in water. Typical carriers include fuller's earth, kaolin clays, silicas and other highly absorbent, readily wettable, inorganic diluents. Typical wetting, dispersing or emulsifying agents include, for example, aryl and alkylaryl sulfonates and their sodium salts; alkylamide sulfonates, including fatty methyl taurides; alkylaryl polyether alcohols, sulfated higher alcohols, and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. Generally, these finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and can consist entirely of the fungicide with a liquid or solid emulsifying agent, or can also contain a liqid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried in relatively course particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, can also be used. All of those techniques for formulating and applying fungicides are well known in the art.

The percentages by weight of the fungicide can vary according to the manner in which the composition is to be applied and the particular type of formulation, but in general comprise 0.05% to 95% of the toxicant by weight of the fungicidal composition, typically depending on whether the composition is intended for direct application or dilution prior to application. The compounds are typically applied at rates in the range of about from 0.1 to 5 kg/hectare, preferably 0.2 to 3 kg/hectare.

The fungicidal compositions can be formulated and applied with other active ingredients, including other fungicides, insecticides, nematocides, bactericides, plant growth regulators, fertilizers, etc.

A further understanding of the invention can be had in the following non-limiting Examples, wherein, unless expressly stated to the contrary, all temperatures and temperature ranges refer to the centigrade or Celcius system and the term "ambient" or "room temperature" refers to about 20° to 25° C. The term "percent" refers to weight percent and the term "mole" or "moles" refers to gram moles. The term "equivalent" refers to a reagent equal in moles, to the moles of the preceding or succeeding reactant recited in that example in terms of finite moles or finite weight or volume. Unless expressly stated to the contrary, E- and Z-isomers are generated where appropriate and are not separated. Also, unless expressly stated to the contrary, geometric isomer and racemic mixtures are used as starting materials and correspondingly isomer mixtures are obtained as products.

EXAMPLES

EXAMPLE 1

1-(2,4-Dichlorophenoxy)-3,3-dimethylbutan-2-one

In this example, 8.4 g (0.155 mol) of sodium methoxide was added to a solution containing 24.5 g (0.15 mol) of 2,4-dichlorophenol in 150 ml of methanol at room temperature. The mixture was stirred for 10 minutes and then a solution containing 26.7 g (0.15 mol) of alphabromopinacolone was added dropwise. The resulting mixture was heated under reflux for 6 hours, then stirred overnight (about 15 hours) at room temperature and then filtered. The filtrate was concentrated by evaporation and the oily residue was dissolved in diethyl ether. The ether phase was washed sequentially with equal volumes of aqeuous 1N. sodium hydroxide, water, saturated aqueous sodium chloride, then dried over magnesium sulfate and filtered. The filtrate was concentrated in vacuo. Trituration of the residue with hexanes yielded the title compound as a white solid, 22.9 g, m.p. 63.0°-64.0° C.

EXAMPLE 2

3-[2-(2,4-dichlorophenoxy)-3-oxo-4,4-dimethylpent-1-enyl]pyridine

In this example 5.0 grams (0.019 mole) of t-butyl 2,4-dichlorophenoxymethyl ketone and 2.1 ml (0.022 mole) of 3-pyridinecarboxaldehyde are added to 50 ml of methanol containing 0.1 g of sodium methoxide. The mixture is then stirred at room temperature for 5 hours and then evaporated to remove the methanol solvent, affording a semi-solid residue. The residue was then partitioned between diethyl ether and water. The separated ethyl ether phase was then extracted sequentially with 1N. aqueous sodium hydroxide, washed three times with water and then one time with brine. The diethyl ether phase was then dried over magnesium sulfate, filtered, then concentrated in vacuo affording a yellow oil. The yellow oil was then chromatographed on silica gel eluting with hexane ethyl acetate mixtures. The chromatographed fractions were combined by a thin layer chromatographed profile and then concentrated by evaporation affording the title compound as a viscous oil, 5.9 g.

EXAMPLE 3

3-[2-(2,4-dichlorophenoxy)-3-hydroxy-4,4-dimethylpent-1-enyl]pyridine

In this example, 0.49 g (0.0129 mole) of sodium borohydride was added portion-wise to a mixture containing 20 ml of methanol and 4.5 g (0.0129 mole) of 3-[2-(2,4-dichlorophenoxy)-3-oxo-4,4-dimethylpent-1-enyl]pyridine at 0° C. with stirring. The mixture was stirred at 0° C. for 15 minutes, then quenched by the addition of water. The mixture was then diluted with more water and then extracted twice with methylene chloride. The methylene chloride extracts were washed with water twice, dried over magnesium sulfate, filtered, then concentrated under vacuum affording a foam. The foam was dissolved in ethyl acetate, then chromatographed by flash column chromatography (silica gel) eluting with hexane and ethyl acetate mixtures. The product fractions were combined, concentrated and the residue recrystallized from methanol and water affording white crystals of the title compound mp 79.0°-81.5° C.

EXAMPLE 4

Similarly, by following the procedures set forth in Examples 1-3 but using the appropriately substituted phenol and ketone starting materials the following illustrative compounds can be prepared.

3-[2-(2,6-dichlorophenoxy)-3-hydroxy-4,4-dimethylpent-1-enyl]pyridine;
3-[2-(2,4-difluorophenoxy)-3-hydroxy-4,4-dimethylpent-1-enyl]pyridine;
3-[2-(4-fluorophenoxy)-3-hydroxy-4,4-dimethylpent-1-enyl]pyridine;
3-[2-(2,4-dibromophenoxy)-3-hydroxy-4,4-dimethylpent-1-enyl]pyridine;
3-[2-(2,6-diiodophenoxy)-3-hydroxy-4,4-dimethylpent-1-enyl]pyridine;
3-[2-(2-chloro-4-fluorophenoxy)-3-hydroxy-4,4-dimethylpent-1-enyl]pyridine;
3-[2-(2,4-dimethylphenoxy)-3-hydroxy-4,4-dimethylpent-1-enyl]pyridine;
3-[2-(4-hexylphenoxy)-3-hydroxy-4,4-dimethylpent-1-enyl]pyridine;
3-[2-(2,4-dimethoxyphenoxy)-3-hydroxy-4,4-dimethylpent-1-enyl]pyridine;
3-[2-(3-butoxyphenoxy)-3-hydroxy-4,4-dimethylpent-1-enyl]pyridine;
3-[2-(4-phenylphenoxy)-3-hydroxy-4,4-dimethylpent-1-enyl]pyridine;
3-[2-phenoxy-3-hydroxy-4,4-dimethylpent-1-enyl]pyridine;
3-[2-naphthyl-3-hydroxy-4,4-dimethylpent-1-enyl]pyridine;
3-[2-(2-methylnaphthyl)-3-hydroxy-4,4-dimethylpent-1-enyl]pyridine;
3-[2-(2-chloronaphthyl)-3-hydroxy-4,4-dimethylpent-1-enyl]pyridine;
3-[2-(2,4-dichlorophenoxy)-3,5-dihydroxy-4,4-dimethylpent-1-enyl]pyridine;
3-[2-(2,6-dimethylphenoxy)-3,5-dihydroxy-4,4-dimethylpent-1-enyl]pyridine;
3-[2-(4-t-butoxyphenoxy)-3,5-dihydroxy-4,4-dimethylpent-1-enyl]pyridine;
3-[2-(2,4-dichlorophenoxy)-3-hydroxy-4,4-dimethyl-5-chloropentenyl]pyridine;
3-[2-(4-fluorophenoxy)-3-hydroxy-4,4-dimethyl-5-fluoropentenyl]pyridine;
3-[2-(2,4-chlorophenoxy)-3-hydroxy-4,4-dimethyl-5-bromopentenyl]pyridine;
3-[2-(4-chloro-2-methylphenoxy)-3-hydroxy-4,4-dimethylpent-1-enyl]pyridine;
3-[2-(2,4-dichlorophenoxy)-3-hydroxy-4,4-dimethylhex-1-enyl]pyridine;
3-[2-(2,4-difluorophenoxy)-3-hydroxy-4,4-dimethylhex-1-enyl]pyridine;
3-[2-(4-fluorophenoxy)-3-hydroxy-4,4-dimethylhex-1-enyl]pyridine;
3-[2-(2,4-dibromophenoxy)-3-hydroxy-4,4-dimethyloct-1-enyl]pyridine;
3-[2-(2,6-iodophenoxy)-3-hydroxy-4,4-dimethyloct-1-enyl]pyridine;
3-[2-(2-chloro-4-fluorophenoxy)-3-hydroxy-4,4-dimethyloct-1-enyl]pyridine;
3-[2-(2,4-dimethylphenoxy)-3-hydroxy-4,4-dimethyloct-1-enyl]pyridine;
3-[2-(4-hexylphenoxy)-3-hydroxy-4,4-dimethyloct-1-enyl]pyridine;
3-[2-(2,4-dimethoxyphenoxy)-3-hydroxy-4,4-dimethylnon-1-enyl]pyridine;
3-[2-(3-butoxyphenoxy)-3-hydroxy-4,4-dimethylnon-1-enyl]pyridine;
3-[2-(4-phenylphenoxy)-3-hydroxy-4,4-dimethylnon-1-enyl]pyridine;
3-[2-phenoxy-3-hydroxy-4,4-dimethylnon-1-enyl]pyridine;
3-[2-naphthyl-3-hydroxy-4,4,6-trimethylhept-1-enyl]pyridine;
3-[2-(2-methylnaphthyl)-3-hydroxy-4,4,6-dimethylhept-1-enyl]pyridine;
3-[2-(2-chloronaphthyl)-3-hydroxy-4,4,6-dimethylhept-1-enyl]pyridine;
3-[2-(2-bromo-4-chlorophenoxy)-3-hydroxy-3-phenylprop-1-enyl]pyridine;
3-[2-(2-ethyl-4-ethoxyphenoxy)-3-hydroxy-3-phenylprop-1-enyl]pyridine;
3-[2-(4-phenylphenoxy)-3-hydroxy-3-phenylprop-1-enyl]pyridine;
3-[2-(2-butyl-3-chlorophenoxy)-3-hydroxy-3-phenylprop-1-enyl]pyridine; and
3-[7-(2-methylnaphthyl)-3-hydroxy-3-phenylprop-1-enyl]pyridine.

EXAMPLE 5

3-[2-(2,4-dichlorophenoxy)-3-methoxy-4,4-dimethylpent-1-enyl]pyridine

The title compound can be prepared by reacting 0.06 mole of methyl sulfate with 0.1 mole of 3-[2-(2,4-dichlorophenoxy)-3-hydroxy-4,4-dimethylpent-1-enyl]-pyridine in 200 ml tetrahydrofuran at room temperature. The title compound can then be recovered from the reaction product mixture by appropriate laboratory procedures such as, for example, described in the preceding examples set forth herein.

Similarly, the methoxy ethers of the products listed in Example 4 hereinabove, can be prepared by following the same procedures, including, for example:
3-[2-(2,6-dichlorophenoxy)-3-methoxy-4,4-dimethylpent-1-enyl]pyridine;
3-[2-(2,4-difluorophenoxy)-3-methoxy-4,4-dimethylpent-1-enyl]pyridine;
3-[2-(4-fluorophenoxy)-3-methoxy-4,4-dimethylpent-1-enyl]pyridine;
3-[2-(2,4-dibromophenoxy)-3-methoxy-4,4-dimethylpent-1-enyl]pyridine;
3-[2-(2,6-iodophenoxy)-3-methoxy-4,4-dimethylpent-1-enyl]pyridine;
3-[2-(2-chloro-4-fluorophenoxy)-3-methoxy-4,4-dimethylpent-1-enyl]pyridine;
3-[2-(2-bromo-4-chlorophenoxy)-3-methoxy-3-phenylprop-1-enyl]pyridine;
3-[2-(2-ethyl-4-ethoxyphenoxy)-3-methoxy-3-phenylprop-1-enyl]pyridine; and
3-[2-(4-phenylphenoxy)-3-methoxy-3-phenylprop-1-enyl]pyridine.

Similarly, the allyl ethers of the products of Examples 3 and 4 can be prepared by following the same procedure but replacing 0.06 mole of methyl sulfate with 0.12 mole of allyl chloride and using the appropriate 3-hydroxy starting material. Such allyl ethers include:
3-[2-(2,4-dichlorophenoxy)-3-allyloxy-4,4-dimethylpent-1-enyl]pyridine;
3-[2-(2,4-dimethylphenoxy)-3-allyloxy-4,4-dimethylpent-1-enyl]pyridine;
3-[2-(4-hexylphenoxy)-3-allyloxy-4,4-dimethylpent-1-enyl]pyridine;
3-[2-(2,4-dimethoxyphenoxy)-3-allyloxy-4,4-dimethylpent-1-enyl]pyridine;
3-[2-(3-butoxyphenoxy)-3-allyloxy-4,4-dimethylpent-1-enyl]pyridine;
3-[2-(4-phenylphenoxy)-3-allyloxy-4,4-dimethylpent-1-enyl]pyridine;

3-[2-phenoxy-3-allyloxy-4,4-dimethylpent-1-enyl]pyridine;

3-[2-naphthyl-3-allyloxy-4,4-dimethylpent-1-enyl]pyridine;

3-[2-(2-methylnaphthyl)-3-allyloxy-4,4-dimethylpent-1-enyl]pyridine;

3-[2-(2-chloronaphthyl)-3-allyloxy-4,4-dimethylpent-1-enyl]pyridine; and

3-[2-(2,4-dichlorophenoxy)-3-allyloxy-5-hydroxy-4,4-dimethyl-pent-1-enyl]pyridine.

Similarly, the 3-chloroallyloxy ethers of the products of Examples 3 and 4 can be prepared by the same procedure but replacing 0.06 mole of methyl sulfate with 0.12 mole of 1,3-dichloropropene (i.e. ClHC=CHCH$_2$Cl). Such ethers include:

3-[2-(2,4-dichlorophenoxy)-3-(3-chloroallyloxy)-4,4-dimethylpent-1-enyl]pyridine;

3-[2-(2,4-dimethylphenoxy)-3-(3-chloroallyloxy)-4,4-dimethylpent-1-enyl]pyridine;

3-[2-(4-hexylphenoxy)-3-(3-chloroallyloxy)-4,4-dimethylpent-1-enyl]pyridine;

3-[2-(2,4-dimethoxyphenoxy)-3-(3-chloroallyloxy)-4,4-dimethylpent-1-enyl]pyridine;

3-[2-(3-butoxyphenoxy)-3-(3-chloroallyloxy)-4,4-dimethylpent-1-enyl]pyridine;

3-[2-(4-phenylphenoxy)-3-(3-chloroallyloxy)-4,4-dimethylpent-1-enyl]pyridine;

3-[2-phenoxy-3-(3-chloroallyloxy)-4,4-dimethylpent-1-enyl]pyridine;

3-[2-naphthyl-3-(3-chloroallyloxy)-4,4-dimethylpent-1-enyl]pyridine;

3-[2-(2-methylnaphthyl)-3-(3-chloroallyloxy)-4,4-dimethylpent-1-enyl]pyridine;

3-[2-(2-chloronaphthyl)-3-(3-chloroallyloxy)-4,4-dimethylpent-1-enhyl]pyridine; and 3-[2-(2,4-dichlorophenoxy)-3-(3-chloroallyloxy)-5-hydroxy-4,4-dimethyl-pent-1-enyl]pyridine.

EXAMPLE 6

3-[2-(2,4-Dichlorophenoxy)-3-acetoxy4,4-dimethylpent-1-enyl]pyridine

The title compound can be prepared by reacting a mixture containing 0.11 mole of acetyl chloride; 0.1 mole of 3-[2-(2,4-dichlorophenoxy)-3-hydroxy-4,4-dimethylpent-1-enyl]pyridine and 0.15 mole of pyridine in 200 ml of toluene at room temperature. The title compound can be recovered from the reaction product mixture by appropriate laboratory procedures such as, for example, described in the preceding examples set forth hereinabove.

Similarly, the acetoxy esters of the products of Example 4 can be prepared by following the same procedure, including, for example:

3-[2-(2,6-dichlorophenoxy)-3-acetoxy-4,4-dimethylpent-1-enyl]pyridine;

3-[2-(2,4-difluorophenoxy)-3-acetoxy-4,4-dimethylpent-1-enyl]pyridine;

3-[2-(2,4-dimethylphenoxy)-3-acetoxy-4,4-dimethylpent-1-enyl]pyridine;

3-[2-(4-hexylphenoxy)-3-acetoxy-4,4-dimethylpent-1-enyl]pyridine;

3-[2-(2,4-dimethoxyphenoxy)-3-acetoxy-4,4-dimethylpent-1-enyl]pyridine;

3-[2-(3-butoxyphenoxy)-3-acetoxy-4,4-dimethylpent-1-enyl]pyridine;

3-[2-(4-phenylphenoxy)-3-acetoxy-4,4-dimethylpent-1-enyl]pyridine;

3-[2-phenoxy-3-acetoxy-4,4-dimethylpent-1-enyl]pyridine;

3-[2-naphthyl-3-acetoxy-4,4-dimethylpent-1-enyl]pyridine;

3-[2-(2-methylnaphthyl)-3-acetoxy-4,4-dimethylpent-1-enyl]pyridine;

3-[2-(2-chloronaphthyl)-3-acetoxy-4,4-dimethylpent-1-enyl]pyridine;

3-[2-(2-bromo-4-chlorophenoxy)-3-acetoxy-3-phenylprop-1-enyl]pyridine;

3-[2-(2-ethyl-4-ethoxyphenoxy)-3-acetoxy-3-phenylprop-1-enyl]pyridine; and

3-[2-(4-phenylphenoxy)-3-acetoxy-3-phenylprop-1-enyl]pyridine.

Similarly, by replacing acetyl chloride with isovaleryl chloride, the corresponding isovaleryloxy esters of the products of Examples 3 and 4 can be prepared, for example:

3-[2-(2,4-dichlorophenoxy)-3-isovaleryloxy-4,4-dimethylpent-1-enyl]pyridine;

3-[2-(2,4-difluorophenoxy)-3-isovaleryloxy-4,4-dimethylpent-1-enyl]pyridine;

3-[2-(4-fluorophenoxy)-3-isovaleryloxy-4,4-dimethylpent-1-enyl]pyridine;

3-[2-phenoxy-3-isovaleryloxy-4,4-dimethylpent-1-enyl]pyridine;

3-[2-naphthyl-3-isovaleryloxy-4,4-dimethylpent-1-enyl]pyridine;

3-[2-(2-methylnaphthyl)-3-isovaleryloxy-4,4-dimethylpent-1-enyl]pyridine;

3-[2-(4-phenylphenoxy)-3-isovaleryloxy-3-phenylprop-1-enyl]pyridine;

3-[2-(2-butyl-3-chlorophenoxy)-3-isovaleryloxy-3-phenylprop-1-enyl]pyridine; and 3-[7-(2-methylnaphthyl)-3-isovaleryloxy-3-phenylprop-1-enyl]pyridine.

EXAMPLE 7

In this example, the compounds of Formula I listed in Table I and the intermediate of Formula A listed in Table II were prepared by following the procedures of Examples 1–3 but using the appropriately substituted phenol and ketone as starting materials. Also for comparison purposes the compounds listed in Table III were prepared from the corresponding compound of Formula I via reduction of the alkene double bond via treatment with zinc dust in acetic acid.

TABLE I

Compounds of the Formula

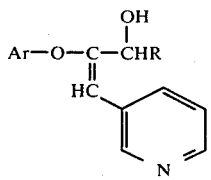

| Compound No. | Ar | R | Carbon Calc. | Carbon Found | Hydrogen Calc. | Hydrogen Found | Nitrogen Calc. | Nitrogen Found | Form | m.p. °C. |
|---|---|---|---|---|---|---|---|---|---|---|
| 1 | 2,4-Cl$_2$φ* | t-butyl | 61.37 | 61.76 | 5.44 | 5.92 | 3.98 | 4.07 | solid | 79–81.5 |
| 2 | 3,4-Cl$_2$φ | t-butyl | 61.03 | 61.52 | 5.41 | 5.60 | 3.95 | 4.25 | solid | 146–148 |
| 3 | 4Clφ | t-butyl | 68.03 | 68.20 | 6.34 | 6.53 | 4.41 | 4.46 | solid | 129–133 |
| 4 | 2,4-Cl$_2$φ | φ | 64.53 | 64.78 | 4.06 | 4.32 | 3.76 | 3.81 | oil | — |
| 5 | 2-CH$_3$—4-Clφ | t-butyl | 68.77 | 68.67 | 6.68 | 6.64 | 4.22 | 4.21 | solid | 114–116 |

*φ = phenyl

TABLE II

Compounds of the Formula

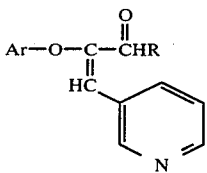

| Compound No. | Ar | R | Carbon Calc. | Carbon Found | Hydrogen Calc. | Hydrogen Found | Nitrogen Calc. | Nitrogen Found | Form | m.p. °C. |
|---|---|---|---|---|---|---|---|---|---|---|
| 6 | 2,4-Cl$_2$φ* | t-butyl | 61.73 | 63.55 | 4.89 | 5.19 | 4.00 | 4.43 | oil | — |
| 7 | 3,4-Cl$_2$φ | t-butyl | 61.73 | 61.84 | 4.89 | 5.44 | 4.00 | 3.62 | solid | 83–85 |
| 8 | 2,4-Cl$_2$φ | φ | 67.81 | 65.36 | 3.7 | 3.68 | 3.95 | 3.94 | solid | 115.5–117.0 |

*φ = phenyl

TABLE III

Compounds of the Formula

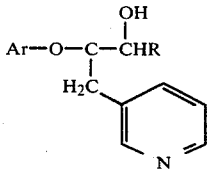

| Compound No. | Ar | R | Carbon Calc. | Carbon Found | Hydrogen Calc. | Hydrogen Found | Nitrogen Calc. | Nitrogen Found | Form | m.p. °C. |
|---|---|---|---|---|---|---|---|---|---|---|
| C-1 | 2,4-Cl$_2$φ* | t-butyl | 61.03 | 64.80 | 5.97 | 6.41 | 3.95 | 4.21 | solid | 119–122 |

*φ = phenyl

EXAMPLE 8

In this example, the compounds of Example 7, Tables I, II and III, were tested for effectiveness against a number of different fungi organisms. The particular organisms and test procedures used are described below. In these tests the compounds were compared against check plants which were also sprayed with the test vehicle but without the test compounds. Generally, two replicates were used for each test compound and the results given in Table IV hereinbelow is the average of the replicates.

Bean Powdery Mildew

The compounds of the invention were tested for the control of the Bean Powdery Mildew organism *Erysiphe polygoni*. Seedling bean plants were sprayed with a 250-ppm solution of the test compound in acetone, water and a nonionic emulsifier. The sprayed plants were then inoculated 1 day later with the organism. The plants were maintained for 10 days at temperatures of 68° F. at night with daytime temperatures of 72° to 80° F.; relative humidity was maintained at 40% to 60%. The percent disease control provided by a given test compound was based on the percent disease reduction relative to the untreated check plants.

Tomato Late Blight

The compounds of the invention were tested for the preventative control of the Tomato Late Blight organism *Phytophthora infestans*. Five- to six-week-old tomato plants were sprayed with a 250-ppm suspension of the test compound in acetone, water and a nonionic emulsifier. The sprayed plants were then inoculated 1 day later with the organism, placed in an environmental chamber and incubated at 66° to 68° F. and 100% relative humidity for at least 16 hours. Following the incubation, the plants were maintained in a greenhouse for approximately 7 days. The percent disease control provided by a given test compound was based on the percent disease reduction relative to untreated check plants.

Grape Downy Mildew

The compounds of the invention were tested for the control of the Grape Downy Mildew organism *Plasmopara viticola*. Seven-week old *Vitis vinifera* cultivar Emperor grape seedlings approximately 3 inches tall were used as hosts. The plants were sprayed with a 250-ppm solution of the test compound in acetone and water containing a small amount of nonionic emulsifier. The plants were dried, inoculated with a spore suspension of the organism, placed in a humid environmental chamber and incubated at 66° to 68° F. and about 100% relative humidity. After incubation for 2 days, the plants were placed in standing water in a greenhouse at 66°-68° F. for four days and then placed in an environmental chamber for 48 hours at 100% relative humidity. The plants are then removed from the chamber, dried and then evaluated for the amount of disease control. The percent disease control provided by a given test compound was based on the percent disease reduction relative to untreated check plants.

Bean Rust

The Bean Rust test was made using pinto bean plants and was conducted as an eradicant test. The pathogen was *Uromyces phaseoli tipica*. The plants were inoculated with the pathogen and then incubated in an environmental chamber for approximately 24 hours at 100% relative humidity and a temperature of 68° to 70° F. The plants were then removed from the chamber, allowed to dry. The pinto bean plants were then sprayed with a 250-ppm solution of the test compound in an acetone-water mixture containing a small amount nonionic emulsifier. The plants were dried and then maintained in a greenhouse at a 40 to 80% relative humidity and 66° to 72° F. for 7 days. The plants were then evaluated for the percent disease control. The percent disease control provided by a given test compound was based on the percent disease reduction relative to untreated check plants.

Rice Blast

Compounds of this invention were tested for control of the Rice Blast organism *Piricularia oryzae*, using 10- to 14-day old rice plant seedlings (Calrose M-9 variety). Seedling plants were sprayed with a 625-ppm solution of the test compound in acetone, water and a nonionic emulsifier. The sprayed plants were inoculated 1 day later with the organism in an environmental chamber. After inoculation, the plants were kept in an environmental chamber for about 48 hours under conditions of about 72° to 75° F. and about 100% relative humidity. Following the incubation period, the plants were placed in a greenhouse with a temperature of about 72° F. and maintained with bottom watering for about 12 to 16 days. The percent disease control provided by a given test compound is based on a comparison of the percentage disease relative to the percent disease development on the untreated check plants.

The results of the above tests are reported in Table IV hereinbelow, wherein:

$$\% \text{ Control} = 100 \times \left( \frac{\% \text{ disease in treated plants}}{\% \text{ disease in check}} \right)$$

TABLE IV

Preventative Fungicidal Activity
% Control

| Compound No. | GDM | TLB | CLB | TEB | BR | BPM | RB |
|---|---|---|---|---|---|---|---|
| 1 | 16 | 54 | 97 | — | 100 | 100 | 22 |
| 2 | 80 | 54 | 83 | 79 | 0 | 100 | 8 |
| 3 | 53 | 14 | 90 | 52 | 46 | 100 | 0 |
| 4 | 57 | 61 | 94 | 96 | 0 | 100 | 33 |
| 5 | 46 | 57 | 100 | 100 | 19 | 100 | 25 |
| 6 | 7 | 27 | 85 | 39 | 98 | 100 | 24 |
| 7 | 20 | 10 | 0 | 8 | 0 | 100 | 18 |
| 8 | 24 | 35 | 83 | — | 0 | 100 | 22 |
| C-1 | 0 | 4 | 54 | 50 | 0 | 100 | 0 |

GDM - Grape Downy Mildew (*Plasmopara viticola*)
TLB - Tomato Late Blight (*Phytophthora infestans*)
CLB - Celery Late Blight (*Septoria apii*)
TEB - Tomato Early Blight (*Alternaria solani cnoidia*)
BR - Bean Rust (*Uromyces phaseoli tipica*)
BPM - Bean Powdery Mildew (*Erysiphe polygoni*)
RB - Rice Blast (*Piricularia oryzae*)

As can be seen from the results given in Table IV all of the compounds tested exhibited excellent activity against Bean Powdery Mildew pathogen. All of the compounds of the present invention further exhibited very substantially superior activity against Celery Late Blight pathogen as compared with comparison compound C-1. Moreover, the closest compound of the present invention (i.e. compound No. 1) to compound C-1 exhibited 100% eradication of Bean Rust pathogen whereas compound C-1 exhibited zero control.

EXAMPLE 9

In this example compound No. 1 (Ar is 2,4-dichlorophenyl, R is t-butyl and $R^1$ is hydrogen) and its ketone precursor, compound No. 6, were tested for low dosage preventative fungicidal action with respect to Tomato Early Blight, Celery Late Blight and Bean Powdery Mildew. These tests were conducted in the same manner as described in Example 8 with the exception of the amount of the dosage. The dosages used and the results of these tests are summarized in Table V hereinbelow.

TABLE V

Low Dosage Fungicidal Activity

| Compound No. | Dosage ppm | Fungal Disease % Control | | |
|---|---|---|---|---|
| | | TEB | CLB | BPM |
| 1 | 250 | 71 | 100 | |
| 1 | 100 | 57 | 98 | |
| 1 | 40 | 27 | 69 | |
| 1 | 16 | — | — | 100 |

TABLE V-continued

| | Low Dosage Fungicidal Activity | | | |
|---|---|---|---|---|
| | Dosage | Fungal Disease % Control | | |
| Compound No. | ppm | TEB | CLB | BPM |
| 1 | 6.4 | — | — | 100 |
| 1 | 2.5 | — | 0 | 100 |
| 1 | 1.0 | — | — | 96 |
| 1 | *ED 50/90 | 94/580 | 30/64 | 0.1/0.5 |
| 6 | 250 | 22 | 89 | |
| 6 | 100 | 23 | 80 | |
| 6 | 40 | 34 | 68 | |
| 6 | 16 | | — | 88 |
| 6 | 6.4 | | — | 60 |
| 6 | 2.5 | | — | 25 |
| 6 | ED 50/90 | — | 12/280 | 1/3 |

*ED 50/90 are calculated values of the dosage rate (ppm) needed to obtain 50% control and 90%. The lower ED 50/90 value, the better the activity.

As can be seen from the above table, compound No. 1 has superior preventative activity over compound No. 6 with respect to Tomato Late Blight, Celery Late Blight and Bean Powdery Mildew and has particularly good preventative activity with respect to Bean Powdery Mildew.

Obviously, many modifications and variations of the invention, described hereinabove and below, can be made without departing from the essence and scope thereof.

What is claimed is:

1. A compound having the formula

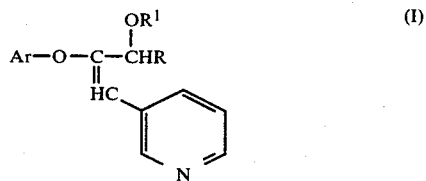

wherein

Ar is phenyl; substituted phenyl having one or two substituents independently selected from the group of halo, lower alkyl, or lower alkoxy;

R is phenyl or the group $-C(CH_3)_2CH_2)R^2$ wherein $R^2$ is hydrogen lower alkyl having 1 through 4 carbon atoms, hydroxy, or halo; and $R^1$ is lower alkyl, benzyl, allyl, or haloallyl having one or two halo substituents independently selected from the group of fluoro, chloro, bromo or iodo;

and non-phytotoxic salts thereof.

2. The compound of claim 1 wherein R is phenyl.

3. The compound of claim 1 wherein R is the group

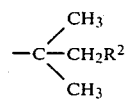

wherein $R^2$ is as defined in claim 1.

4. The compound of claim 3 wherein $R^2$ is hydrogen.

5. The compound of claim 4 wherein $R^1$ is lower alkyl or allyl.

6. The compound of claim 1 wherein Ar is 2,4-dichlorophenyl.

7. The compound of claim 1 wherein Ar is 4-chlorophenyl.

8. The compound of claim 1 wherein $R^1$ is lower alkyl.

9. The compound of claim 1 wherein $R^1$ is allyl.

10. The compound of claim 1 wherein $R^1$ is haloallyl.

11. The compound of claim 1 wherein $R^1$ is benzyl.

12. The compound of claim 1 wherein said compound is a cis isomer with respect to the 1-alkenyl double bond.

13. The compound of claim 1 wherein said compound is a trans isomer with respect to the 1-alkenyl double bond.

14. The compound of claim 5 wherein said compound is a cis isomer with respect to the 1-alkenyl double bond.

15. The compound of claim 5 wherein said compound is a trans isomer with respect to the 1-alkenyl double bond.

16. A method for controlling fungi which comprises applying a fungicidally effective amount of the compound of claim 1, to said fungi or to their habitat.

17. A method for controlling fungi which comprises applying a fungicidally effective amount of the compound of claim 5 to said fungi or their habitat.

18. A fungicidal composition comprising a fungicidally effective amount of the compound of claim 1 in combination with a compatible carrier.

19. A fungicidal composition comprising a fungicidally effective amount of the compound of claim 5 in combination with a compatible carrier.

* * * * *